United States Patent

Koehler

(10) Patent No.: US 10,010,723 B2
(45) Date of Patent: Jul. 3, 2018

(54) THERAPY SYSTEM FOR DEPOSITING ENERGY

(71) Applicant: Profound Medical Inc., Mississauga (CA)

(72) Inventor: Max Oskar Koehler, Eindhoven (NL)

(73) Assignee: Profound Medical Inc., Mississauga, ON (CA)

(*) Notice: Subject to any disclaimer, the term of this patent is extended or adjusted under 35 U.S.C. 154(b) by 88 days.

(21) Appl. No.: 14/784,707

(22) PCT Filed: Apr. 4, 2014

(86) PCT No.: PCT/EP2014/056763
§ 371 (c)(1),
(2) Date: Oct. 15, 2015

(87) PCT Pub. No.: WO2014/170138
PCT Pub. Date: Oct. 23, 2014

(65) Prior Publication Data
US 2016/0051845 A1 Feb. 25, 2016

Related U.S. Application Data

(60) Provisional application No. 61/893,369, filed on Oct. 21, 2013.

(30) Foreign Application Priority Data

Apr. 18, 2013 (EP) .................................... 13164279

(51) Int. Cl.
*A61B 5/055* (2006.01)
*A61N 7/02* (2006.01)
(Continued)

(52) U.S. Cl.
CPC ................ *A61N 7/02* (2013.01); *A61B 5/015* (2013.01); *A61B 5/055* (2013.01); *A61B 90/37* (2016.02);
(Continued)

(58) Field of Classification Search
CPC .......... A61B 18/18; A61B 2017/00084; A61B 2090/374; A61B 5/015; A61B 5/055;
(Continued)

(56) References Cited

U.S. PATENT DOCUMENTS 4,375,220 A 3/1983 Matvias
6,575,969 B1 6/2003 Rittman et al.
(Continued)

FOREIGN PATENT DOCUMENTS

DE 2407559 A1 8/1975
EP 2332614 A1 6/2011
(Continued)

OTHER PUBLICATIONS

Partanen et al "Reduction of Peak Acoustic Pressure and Shaping of Heated Region by Use of Multifoci . . . " Med. Phys. 40 (1) Jan. 2013.

*Primary Examiner* — Mark Remaly
(74) *Attorney, Agent, or Firm* — Intrinsic Law Corp.

(57) ABSTRACT

The invention relates to a system in the field of MR guided thermal treatment and more specifically to the temperature control. In the invention an MR and a thermal treatment system are combined. The thermal treatment system is configured to apply thermal treatment pulses to a subject. The prevent overheating of healthy tissue, the thermal treatment pulses are spaced by a cool-down period. The end of the cool-down period is determined by temperature measurements performed during the cool-down period.

15 Claims, 2 Drawing Sheets

(51) Int. Cl.
*A61N 5/02* (2006.01)
*A61B 5/01* (2006.01)
*A61B 90/00* (2016.01)
*A61B 18/18* (2006.01)
*A61B 17/00* (2006.01)

(52) U.S. Cl.
CPC .............. *A61N 5/025* (2013.01); *A61B 18/18* (2013.01); *A61B 2017/00084* (2013.01); *A61B 2090/374* (2016.02); *A61N 5/02* (2013.01)

(58) Field of Classification Search
CPC .......... A61B 90/37; A61N 5/02; A61N 5/025; A61N 7/02
See application file for complete search history.

(56) References Cited

U.S. PATENT DOCUMENTS

| | | |
|---|---|---|
| 6,669,638 B1 | 12/2003 | Miller et al. |
| 6,735,461 B2 | 5/2004 | Vitek et al. |
| 7,211,044 B2 | 5/2007 | Mast et al. |
| 7,367,944 B2 | 5/2008 | Rosemberg et al. |
| 7,771,418 B2 | 8/2010 | Chopra et al. |
| 2009/0036773 A1 | 2/2009 | Lau |
| 2011/0077557 A1 | 3/2011 | Wing et al. |
| 2012/0101412 A1 | 4/2012 | Vortman et al. |
| 2012/0238873 A1* | 9/2012 | Lacoste .................... A61N 7/02 600/439 |
| 2014/0005523 A1* | 1/2014 | Kohler .................... A61B 5/055 600/411 |

FOREIGN PATENT DOCUMENTS

| | | |
|---|---|---|
| EP | 2500740 A1 | 9/2012 |
| JP | 1992352971 | 12/1992 |
| JP | 2006520622 A | 9/2006 |
| WO | 2010029474 A1 | 3/2010 |
| WO | 2011021106 A1 | 2/2011 |

* cited by examiner

THERAPY SYSTEM FOR DEPOSITING ENERGY

CROSS REFERENCE TO RELATED APPLICATIONS

This application is a U.S. national phase application of International Application No. PCT/EP2014/056763 filed on Apr. 4, 2014, which claims the benefit of EP Application Serial No. 13164279.5 filed Apr. 18, 2013 and U.S. Provisional Application Ser. No. 61/893,369 filed on Oct. 21, 2013, both of which are incorporated herein by reference.

FIELD OF THE INVENTION

The invention relates to a system in the field of MR guided thermal treatment and more specifically to the temperature control.

BACKGROUND OF THE INVENTION

During thermal therapy, energy is deposited into a target zone. Energy can be delivered as sonications in the form of focused ultrasound waves. Sonications are spaced in time by an intersonication delay to minimize thermal build-up. This delay is the cool-down period.

Document WO2010029474A1 describes an MR guided thermal treatment system in which the cool-down period is regulated in dependence of the off-focus maximum temperature during the energy deposit preceding the cool-down period. The maximum temperature rise in the off-focus region is approximately linearly dependent on the deposited energy density and a measurement of the maximum temperature can therefore be used to set the cool-down period. The linear dependence appears to be valid when the temperature decrease due to diffusion of heat can be neglected in the middle of the off-focus ultrasound cone during heating.

Partanen et al Reduction of peak acoustic pressure and shaping of heated region by use of multifoci sonications in MR-guided high-intensity focused ultrasound mediated mild hyperthermia, *Med Phys* 2013 40(1) is about mild hyperthermia, which is in the range of 40-45 degrees Celsius and to be used as an adjuvant for both radiotherapy and chemotherapy. In Partanen et al a binary control algorithm was used for real-time mild hyperthermia feed-back control (abstract, methods). The goal of Partanen et al is to keep temperatures inside the target within a range.

US 2012/101412A1 is about a thermal treatment method, wherein a temperature field in a region encompassing the target tissue and non-target tissue is monitored. Based on the monitored temperature field, the temperature in the non-target tissue is actively adjusted.

WO2011/021106A2 is about a method for performing proton resonance frequency based MR temperature measurements. WO2011/021106A2 tries to solve the problem that during MR thermal imaging a magnetic background field and the magnetic field gradient may change due to various factors unrelated to changes in temperature. These effects may result in incorrect temperature estimates.

SUMMARY OF THE INVENTION

It is an object of the invention to provide an MR guided thermal treatment system that controls the regulation of the cool-down period more accurately.

This object is achieved by a magnetic resonance guided thermal treatment system as described in claim 1.

This object is also achieved by method as described in claim 11 or a computer program product as claimed in claim 12.

An example of a thermal treatment is high intensity focussed ultrasound (HIFU). HIFU ablation therapy is commonly performed by applying several heating events (also called sonications) to a target tissue in a subject. Several sonications are typically needed to ablate the entire volume of interest. Part of the deposited energy is always absorbed in the near field tissues between the external transducer and the target focal plane. These tissues consequently heat up and if an insufficient delay is allowed between the sonification then a thermal build up will occur in these tissues which may eventually cause skin burns or fat layer burns. Therefore, during thermal treatment, sonications can be spaced in time by one or more cool-down periods.

In part due to insulating properties of the fat layer of the subject, thermal build-up therein is of greater concern than for other near field tissues. Commonly, a cool-down period is fixed and predetermined, or based on the applied energy density or based on the observed peak temperature within the water containing near-field tissues. Commonly the peak temperature estimate is done via proton resonance frequency (PRF) thermometry which only works in aqueous tissues due to the absence of hydrogen bonds in fat. Therefore, the peak temperature estimate is obtained with the same imaging sequence as used for monitoring the temperature rise in the target region.

It is an insight of the invention that with an active monitoring of the cooling, a more accurate cooling time could be applied that is not excessive and can take spatial differences in temperature within the fat layer into account. An advantage of this is that it could prevent unnecessary delay of treatment.

According to one aspect of the invention, temperature measurements in fat are performed by using relaxation constant based thermometry. Relaxation constant based thermometry (T1, T2 or T2* based) has shown promise to provide an at least qualitative temperature map of the fat layer. This could be used to monitor when the fat layer within the intended beam path of the next sonication has reached a sufficiently low temperature to allow the next sonication to commence. In case the temperature in fat needs to be similar to the temperature at the start of treatment, a conversion to (qualitative) temperature may not even be needed. If the T1, T2 or T2* measurement is the same as prior to start of therapy, then the temperature should also be.

According to one aspect of the invention the end of the cool-down period is based on a maximum temperature in a region of interest outside the target. According to one embodiment of the invention, the maximum temperature is determined once during the cool-down period. An advantage of this is, that the rest of the cool-down period can be used for other magnetic resonance data acquisitions.

According to another aspect of the invention, spectroscopic techniques or multi-echo techniques could also be utilized to determine the temperature on the border between fat and muscle tissues.

According to one aspect of the invention, temperature dependent magnetic resonance signals are converted to a temperature distribution, which provides spatial differences in temperature. According to another aspect, the temperature distribution is displayed to the user, who can use this for deciding whether or not to continue with the sonications.

According to another aspect of the invention, a user is automatically notified by means of an audio/visual signal when the temperature in a monitored tissue has decreased enough to safely continue with a next sonication.

Temperature decrease of fat during a cool-down period may be relatively slow (typically time constant of around 10 minutes). Therefore, it may not be necessary to constantly measure temperature during cool-down. The time between subsequent temperature measurements in the cool-down period may be used to perform other MR measurements, like for example BOLD imaging, spectroscopy, diffusion weighted imaging.

According to one aspect of the invention, a time point of a temperature measurement is based on a temperature measurement done prior to the cool-down period. For example a maximum temperature in an off-focus region can be used for this purpose. In this way the number of temperature measurements needed in the cool-down may be reduced. The time in the cool-down period, which is not used for temperature measurements may be used to perform other MR measurements.

According to another aspect of the invention the time point of a temperature measurement is based on a previous temperature measurement during the cool-down period. In this way, the sampling frequency may increase as the temperature reaches a threshold below it is safe to start with a new sonication.

According to another aspect of the invention, the fat tissue is actively cooled during the cool-down period, to speed up total treatment time.

These and other aspects of the invention will be apparent from and elucidated with reference to the embodiments described hereinafter.

DETAILED DESCRIPTION OF THE INVENTION

Figure 1:
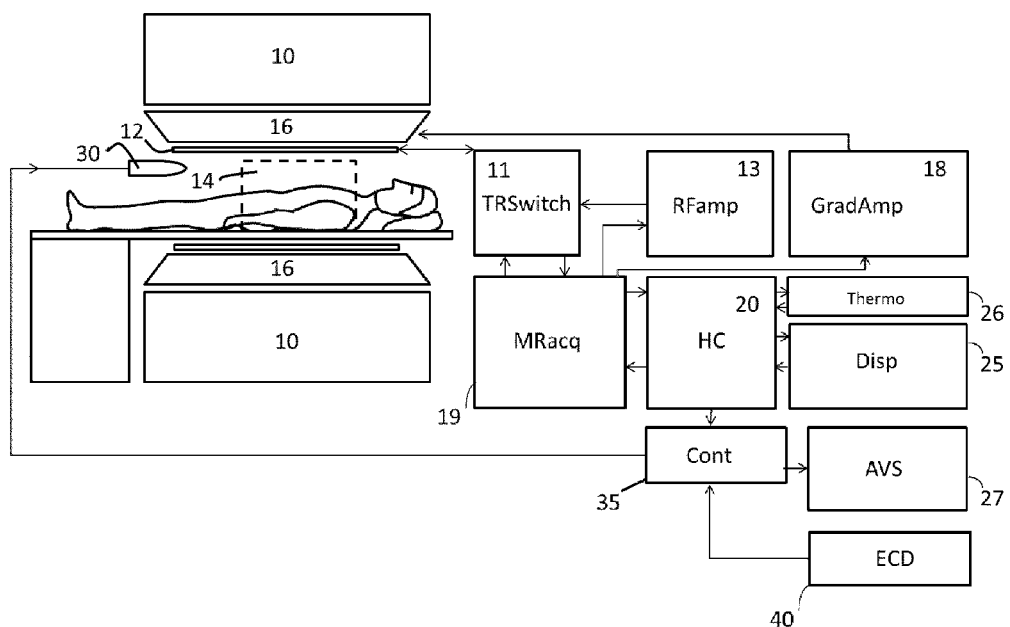
FIG. 1 illustrates diagrammatically a magnetic resonance guided thermal treatment system in which the invention is used.

FIG. 1 illustrates diagrammatically a magnetic resonance guided thermal treatment system in which the invention is used. The MR guided intervention system comprises a magnetic resonance system (not entirely shown) and a thermal therapy system 30. The thermal therapy system 30 could be anything used for MR guided thermal treatment. Thermal treatment could for example be applied by means of HIFU or a microwave antenna. The thermal treatment system is configured for applying thermal treatment pulses, which are spaced by a cool-down period. The thermal treatment system can be turned on or off by a controller (Cont) 35.

The magnetic resonance examination system comprises a main magnet 10 which generates a steady homogeneous main magnetic field within the examination zone 14. This main magnetic field causes a partial orientation of the spins in the object to be examined along the field lines of the main magnetic field. An RF system is provided with one or more RF antennae 12 to emit an RF excitation electromagnetic field into the examination zone 14 to excite spins in the body of the object to be examined. The relaxing spins emit magnetic resonance signals in the RF range which are picked up by the RF antennae 12, notably in the form of RF receiving coils. The RF system 12 is coupled to an Tx/Rx switch (TRSwitch) 11, which in turn is coupled to an RF amplifier (RFamp) 13. Further, gradient coils 16 are provided to generate temporary magnetic gradient fields, notably read gradient pulses and phase encoding gradients. These gradient fields usually are orientated in mutual orthogonal directions and impose spatial encoding on the magnetic resonance signals. Gradient amplifiers (GradAmp) 18 are provided to activate the gradient coils 16 to generate the magnetic gradient encoding fields. The magnetic resonance signals picked up by the RF receiver antennae 12 are applied to an MRI data acquisition system which includes a spectrometer 19. The MR protocol used, determines a contrast type (e.g. T1 weighted or T2 weighted) of the acquired data. The MRI data acquisition system (MRacq) 19 provides the data to a host computer (HC) 20. From the magnetic resonance signals an image can be reconstructed. The image can be displayed on a display (Disp) 25.

In one embodiment, the invention comprises a thermometry module 26, which derives a temperature distribution from the MR signals. The temperature distribution may be a qualitative distribution. The temperature distribution may for example be a result of a comparison between T1, T2 or T2* based signals acquired prior to thermal treatment and signals of the same contrast type acquired during the cool-down period.

In one embodiment the temperature distribution is displayed to a user by means of a display 25. Based on the displayed temperature distribution, the user can decide whether or not to start with a new sonication pulse.

According to one embodiment, the magnetic guided thermal treatment system is configured to check if the temperature dependent magnetic resonance signals acquired during the cool-down period are similar to temperature dependent magnetic resonance signals of the same contrast type acquired prior to the thermal treatment. In case these signals are similar, the temperature will also be similar to the temperature at the start of treatment According to one embodiment, the temperature dependent signals are acquired using relaxation time constant based thermometry (e.g. T1, T2, T2*) in order to determine the temperature or temperature change in a fat layer. These temperatures or temperature changes in a fat layer are used by the thermometry module to determine a temperature distribution.

According to an embodiment of the invention the end of the cool-down period is based on a maximum temperature in a region of interest outside the target. Based on the maximum temperature an estimate can be made about a time needed for the maximum temperature to fall below a pre-set safety threshold. This can for example be done by a model describing tissue temperature change over time. When the maximum temperature is below the pre-set safety threshold, continuation of thermal treatment is considered to be safe. According to one embodiment of the invention, the maximum temperature is determined once during the cool-down period. In this way, the other time during the cool-down period can be used for example for acquisition of other magnetic resonance data, then data needed to determine fat temperature.

According to another embodiment, the temperature dependent signals are acquired using spectroscopic techniques or multi-echo techniques. These techniques are sensitive to temperature changes on the border between muscle tissue and fat. Such techniques could potentially also be applied to monitor cooling during brain ablation through magnetic resonance spectroscopy used to measure temperature-dependent fluctuations in the relative difference between proton resonance frequencies (PRF), such as the chemical shift difference of water and N-Acetylaspartate (NAA), which is often referred to as NAA-PRF spectroscopic thermometry. With the spectroscopic or multi-echo PRF techniques multiple spectral peaks can be resolved and knowing the temperature dependency of the peaks, the frequency difference between the peaks can be converted to an absolute temperature estimate.

According to another embodiment of the invention the magnetic resonance guided thermal treatment system is configured to check if a temperature determined by the temperature dependent magnetic resonance signals fulfils the safety requirements for continuation of the sonications. This could for example be done by checking if the maximum temperature value within a region or volume of interest is below a pre-set safety threshold. It could also be a spatially dependent comparison of a temperature 2D/3D image to a pre-set safety threshold as well. If one or more temperature values of interest fulfill the safety requirements for continuation of the sonication, a user is notified by means of an audio and/or visual signal (AVS) 27, which could also be part of the display 25. As the comparison can be for an image, the notification can come at different time points for different intended sonication positions with different cross-sections with the near field. This means that a sonication will only heat up the part of the near-field or fat, that intersects with the beam path. If the beam path of the planned sonication in question has a sufficiently low temperature then it may be sonicated even if other areas within the near field have a too high temperature.

In one embodiment, the tissue is actively cooled during the cool-down period, to speed up total treatment time by means of an external cooling device (ECD) 40. Cooling duration, temperature of a cooling medium or flow rate of the cooling medium are controlled based on the magnetic resonance signals by means of a controller. The controller could be part of the controller 35.

Figure 2:
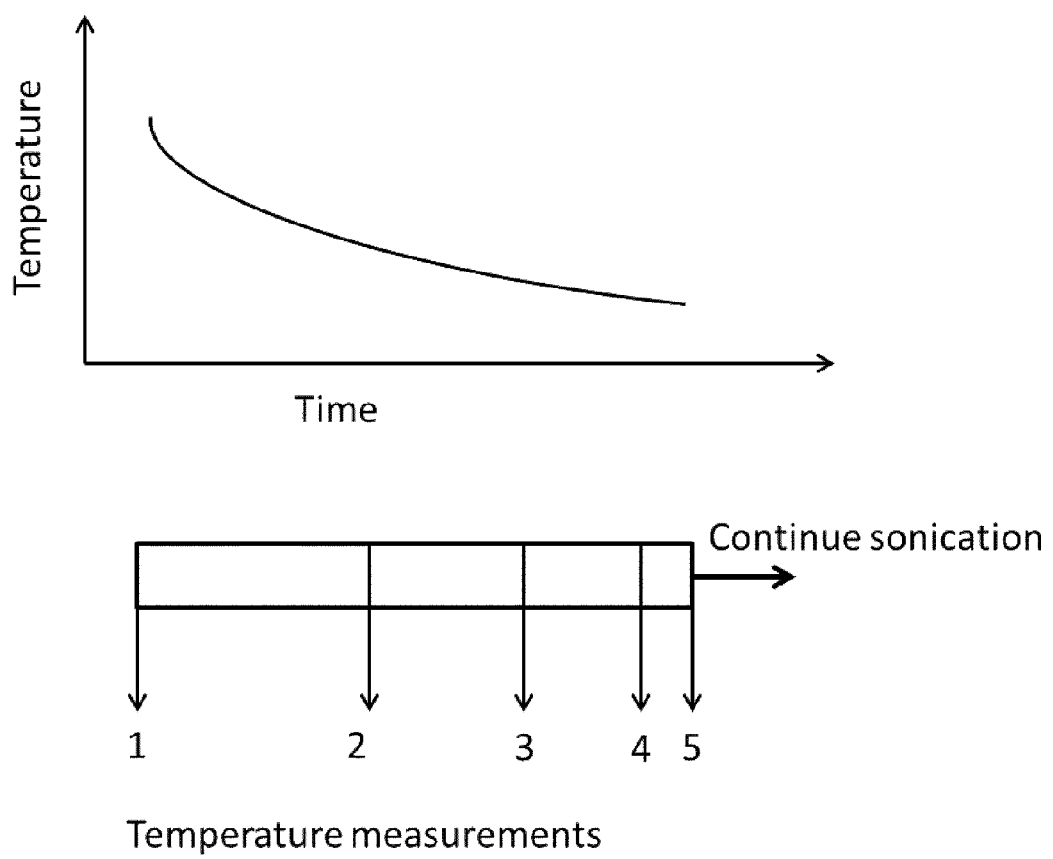
FIG. 2 schematically shows an example of a measurement schedule during a cool-down period.

FIG. 2 schematically shows an example of a measurement schedule during a cool-down period. Based on a temperature measurement just before the cool-down period 1 the time point of the first temperature measurement in the cool-down period 2 is determined. Then measurement 1 or 2 or a combination of both may be used to determine the time point of measurement 3. In this way, the sampling frequency may increase as the temperature reaches a threshold below it is safe to start with a new sonication.

Whilst the invention has been illustrated and described in detail in the drawings and foregoing description, such illustrations and description are to be considered illustrative or exemplary and not restrictive; the invention is not limited to the disclosed embodiments and can be used for temperature control within the field of MR guided thermal treatment.

The invention claimed is:

1. A magnetic resonance guided thermal treatment system, comprising:
a thermal treatment system configured to apply thermal treatment pulses to a target in a subject, wherein the thermal treatment pulses are spaced in time by a cool-down period,
a magnetic resonance system, configured to perform temperature measurements on the subject by acquiring temperature dependent magnetic resonance signals,
a controller configured for switching the magnetic resonance guided thermal treatment system on or off, based on temperature-dependent magnetic resonance signals, wherein the magnetic resonance guided thermal treatment system is configured to determine an end of the cool-down period based on the temperature measurements in fat outside the target performed during the cool-down period, wherein at least one of a temperature or temperature change is determined based on relaxation time constant based thermometry, the magnetic resonance guided thermal treatment system further configured to determine, during the cool-down period, a time point of a subsequent temperature measurement based on a previous temperature measurement such that the magnetic resonance guided thermal treatment system increases a temperature measurement sampling frequency as the temperature reaches a maximum temperature threshold.

2. The magnetic resonance guided thermal treatment system as set forth in claim 1, wherein the end of the cool-down period is determined based on a maximum temperature in the fat in a region of interest.

3. The magnetic resonance guided thermal treatment system as set forth in claim 1, further configured to determine a time point of the temperature measurement during the cool-down period based on the temperature-dependent magnetic resonance signals acquired prior to the cool-down period.

4. The magnetic resonance guided thermal treatment system as set forth in claim 1, further configured to compare one or more temperature values of interest determined by the temperature-dependent magnetic resonance signals with one or more pre-set safety thresholds for the one or more temperature values of interest, wherein the magnetic guided thermal treatment system also comprises:
an audio device configured to provide an audio signal for notifying a user when the one or more temperature values of interest are below the one or more pre-set safety thresholds.

5. The magnetic resonance guided thermal treatment system as set forth in claim 1, further configured to determine if temperature dependent magnetic resonance signals acquired prior to treatment are similar to temperature dependent magnetic resonance signals of a same contrast type acquired during the cool-down period.

6. The magnetic resonance guided thermal treatment system as set forth in claim 1, further configured to determine temperature or temperature change on a border between fat and muscle tissues or in brain, based on spectropic techniques, or multi-echo techniques.

7. A computer implemented method for determining an end of a cool-down period in a thermal treatment process, the method comprising:
applying thermal treatment pulses to a subject, using a computer, wherein the thermal treatment pulses are spaced in time by a cool-down period;
performing temperature measurements on the subject by acquiring temperature dependent magnetic resonance signals during the cool-down period, using the computer, to determine the end of the cool-down period, the temperature dependent magnetic resonance signals corresponding to a temperature;
determining, during the cool-down period, a time point of a subsequent temperature measurement based on a previous temperature measurement such that the computer increases a temperature measurement sampling frequency as the temperature reaches a maximum temperature threshold; and controlling, using the computer, the cool-down period based on the temperature measurements in fat outside the target performed during the cool-down period.

8. A computer program product comprising:
executable instructions embodied on a non-transitory computer readable storage medium that, when executed by a computer, cause the computer to perform a computer implemented method for determining an end of a cool-down period in a thermal treatment process, the method comprising:
  applying thermal treatment pulses to a subject, using the computer, wherein the thermal treatment pulses are spaced in time by a cool-down period;
  performing temperature measurements on the subject by acquisition of acquiring temperature dependent magnetic resonance signals during the cool-down period, using the computer, to determine the end of the cool-down period, the temperature dependent magnetic resonance signals corresponding to a temperature;
  determining, during the cool-down period, a time point of a subsequent temperature measurement based on a previous temperature measurement such that the computer increases a temperature measurement sampling frequency as the temperature reaches a maximum temperature threshold; and
  controlling, using the computer, the cool-down period based on the temperature measurements in fat outside the target performed during the cool-down period.

9. The magnetic resonance guided thermal treatment system as set forth in claim 1 further configured to compare one or more temperature values of interest determined by the temperature-dependent magnetic resonance signals with one or more pre-set safety thresholds for the one or more temperature values of interest, wherein the magnetic guided thermal treatment system also comprises:
  a display configured to provide a visual signal for notifying a user when the one or more temperature values of interest are below the one or more pre-set safety thresholds.

10. A magnetic resonance guided thermal treatment system, comprising:
  a thermal treatment system configured to apply thermal treatment pulses to a target in a subject, wherein the thermal treatment pulses are spaced in time by a cool-down period,
  a magnetic resonance system, configured to perform temperature measurements on the subject by acquiring temperature-dependent magnetic resonance signals,
  a controller configured for switching the magnetic resonance guided thermal treatment system on or off, based on temperature-dependent magnetic resonance signals,
  wherein the magnetic resonance guided thermal treatment system is configured to determine an end of the cool-down period based on the temperature measurement in fat outside the target performed during the cool-down period, wherein at least one of a temperature or temperature change is determined based on proton resonance frequency (PRF) thermometry signals, the magnetic resonance guided thermal treatment system further configured to determine, during the cool-down period, a time point of a subsequent temperature measurement based on a previous temperature measurement such that the magnetic resonance guided thermal treatment system increases a temperature measurement sampling frequency as the temperature reaches a maximum temperature threshold.

11. The magnetic resonance guided thermal treatment system as set forth in claim 10, wherein the end of the cool-down period is determined based on a maximum temperature in the fat in a region of interest.

12. The magnetic resonance guided thermal treatment system as set forth in claim 10 further configured to determine a time point of the temperature measurement during the cool-down period, based on the temperature-dependent magnetic resonance signals acquired in a previous temperature measurement.

13. The magnetic resonance guided thermal treatment system as set forth in claim 10 further configured to determine a time point of the temperature measurement during the cool-down period based on the temperature-dependent magnetic resonance signals acquired prior to the cool-down period.

14. The magnetic resonance guided thermal treatment system as set forth in claim 10, further configured to determine if temperature dependent magnetic resonance signals acquired prior to treatment are similar to temperature-dependent magnetic resonance signals of a same contrast type acquired during the cool-down period.

15. The magnetic resonance guided thermal treatment system as set forth in claim 10, further configured to determine temperature or temperature change on a border between fat and muscle tissues or in brain, based on spectropic techniques, or multi-echo techniques.

* * * * *